United States Patent [19]

Neward

[11] Patent Number: 5,112,203
[45] Date of Patent: May 12, 1992

[54] VESSEL VACUUM RELEASE

[76] Inventor: Theodore C. Neward, 521 Scripps Dr., Claremont, Calif. 91711

[21] Appl. No.: 559,621

[22] Filed: Jul. 30, 1990

[51] Int. Cl.⁵ .................. A61F 5/41; F04B 39/08; F16K 31/44
[52] U.S. Cl. .................. 417/440; 251/245; 251/246; 251/322; 251/323
[58] Field of Search .............. 251/245, 246, 244, 242, 251/236, 240, 241, 322, 323, 243, 238, 239; 417/440

[56] References Cited

U.S. PATENT DOCUMENTS

| | | | |
|---|---|---|---|
| 1,307,450 | 6/1919 | Morton | 251/236 X |
| 1,669,419 | 5/1928 | Lunken | 251/241 |
| 2,672,316 | 3/1954 | Persak, Jr. et al. | 251/236 X |
| 2,745,628 | 5/1956 | Carlson | 251/246 X |
| 4,350,477 | 9/1982 | Mazal | 417/478 |
| 4,753,227 | 6/1988 | Yanuck, Jr. | 128/79 |
| 4,856,498 | 8/1989 | Osbon | 128/79 |

Primary Examiner—Leonard E. Smith
Attorney, Agent, or Firm—Lyon & Lyon

[57] ABSTRACT

There is disclosed herein an inexpensive, compact vacuum release which can be operated with one finger. The vacuum release comprises a base which is affixed to the wall of a vessel, a plunger which extends through a channel in the base, a rocker which raises the plunger to an open position in response to finger pressure, and a spring which biases the plunger to a closed position. The plunger has multiple passageways in which air can flow from the atmosphere into the vessel when the plunger is in the open position, and an "O" ring which closes off the air flow when the plunger is in the closed position. Since the vacuum release need not be permanently affixed to the vessel, it can be used on a wide variety of new and existing vessels, and can be replaced at will.

10 Claims, 2 Drawing Sheets

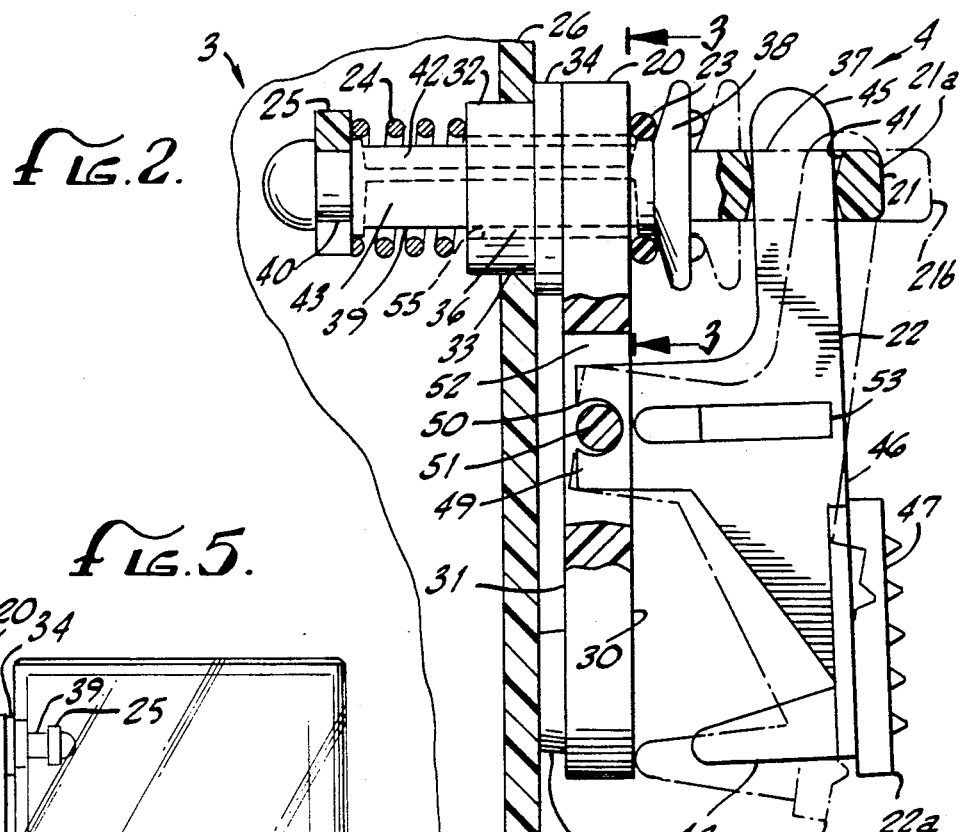

VESSEL VACUUM RELEASE

BACKGROUND OF THE INVENTION

The present invention relates to the field of vacuum pumps, particularly of the hand-held type disclosed in U.S. Pat. Nos. 3,612,722, 4,775,302 and 4,806,084 by the present inventor the disclosures of which are incorporated herein by reference.

Vacuum pumps are generally useful whenever a vacuum is desired, for example, to provide suction. Many types of pumps have been devised, but they often suffer from such drawbacks as complexity, expense, excessive bulk, inability to pull a suitable vacuum, and the like. The vacuum pumps of the aforesaid patents have significantly solved the need for a vacuum pump which is simple, inexpensive, lightweight, compact and portable, and one which can pull a useful vacuum.

Such hand-held vacuum pumps are particularly useful in various industries, such as the automotive industry for vacuum testing and repair, liquid sampling and the like. In the medical field such pumps have been used, for example, with vacuum extraction devices in childbirth, an aid for testing for throat blocking of choking victims, and for other uses. Vacuum pumps manufactured according to the aforesaid patents have the ability to pull a vacuum of, for example, twenty-eight inches of mercury.

Since hand-held vacuum pumps are generally operated by hand, it has been necessary in many cases to use the operator's second hand to operate a vacuum release mechanism. As will be appreciated, this can be cumbersome, especially when operating a vacuum release in a confined environment with limited maneuverability, where there may be fluids or lubricants present, or when there are time restrictions or psychological pressures. Furthermore, it may be desireable to limit the release of the vacuum in a controlled manner, and with minimal finger pressure and dexterity. One example highlighting some of these special circumstances involves the use of a vacuum release on the vessel of a vacuum based penile erection set. This is an emotionally charged situation in which frustration over cumbersome or inconvenient controls may be sufficient to adversely impact the overall usefulness of the device.

One solution to vacuum release problems is disclosed in the aforementioned U.S. Pat. No. 4,806,084. Patent '084 shows and describes a relatively simple vacuum release mechanism attached to the pump, one which can be released relatively easily by a finger of the same hand that operates the pump. However, for some applications, the '084 vacuum release may release the vacuum too quickly or require greater dexterity than possessed by the operator. Moreover, use of the '084 vacuum release could be cumbersome in that the release may not be biased to either the "on" or the "off" position. Hence the operator might become frustrated in unsuccessfully attempting to draw a vacuum in a vessel when the vacuum release was still set to the "off" position from the previous use.

SUMMARY OF THE INVENTION

The present invention is designed to release a vacuum from a vessel in a convenient and controlled manner. It involves an improvement on the aforesaid pump and vessel by enabling the operator to conveniently release the vacuum developed in the vessel using only slight finger pressure.

According to an exemplary embodiment of the invention, a vacuum release comprises a base which is affixed to the wall of a vessel, a plunger which extends through a channel in the base, a rocker which raises the plunger to an open position in response to finger pressure, and a spring which biases the plunger to a closed position. The plunger preferably has multiple passageways in which air or other gasses can flow into a space inside the vessel from the atmosphere or other space outside the vessel when the plunger is in the open position, and an "O" ring which closes off the air flow and permits a vacuum to be maintained in the inside space within the vessel when the plunger is in the closed position.

There are numerous benefits to the present invention. It is relatively compact, uncomplicated, inexpensive to manufacture, and simple to install and operate. The rate of flow of air into the vessel can be readily customized merely by altering the size of the passageways in the plunger. Since the vacuum release need not be permanently affixed to the vessel, it can be used on a wide variety of new and existing pump systems, and can be replaced at will.

Accordingly, it is an object of this invention to provide an improved vacuum release for a vacuum system using a hand-held vacuum pump.

Another object of this invention is to provide a finger operated vacuum release.

Another object of this invention is to provide a finger operated vacuum release having a bias to the "on" position.

Another object of this invention is to provide a finger operated vacuum release for a hand-held vacuum pump.

Another object of this invention is to provide a finger operated vacuum release for a vacuum based medical device.

Another object of this invention is to provide a relatively inexpensive, easily manufactured, compact vacuum release.

Another object of this invention is to provide a vacuum release which releases a vacuum at a controlled rate.

BRIEF DESCRIPTION OF THE DRAWINGS

These and other objects of the present invention will become better understood through a consideration of the following description taken in conjunction with the drawings in which:

FIG. 2 is a cross sectional view showing the assembled vacuum release in an open and a closed position.

FIG. 3 is a portrait cross sectional view of the vacuum release taken along line 3—3 of FIG. 2.

FIG. 5 is a side view of a medical device having a vacuum release.

DETAILED DESCRIPTION OF THE INVENTION

Figure 1:
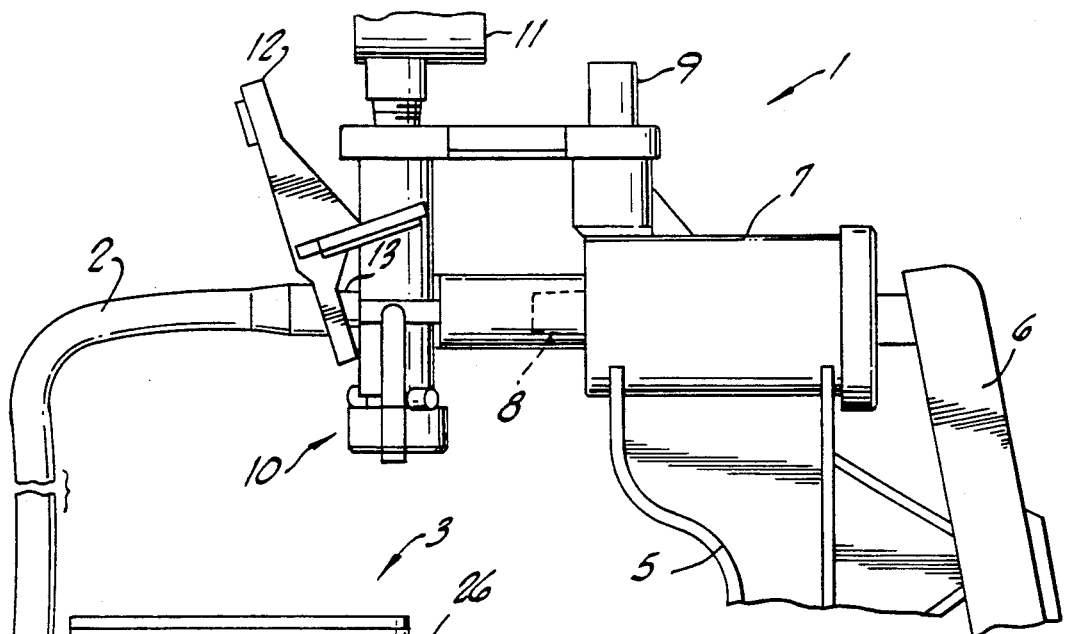
FIG. 1 is a side view of vacuum system showing a pump, a Tee, a tubing remover, tubing, a vessel and a vacuum release.

Turning now to the drawings, FIG. 1 depicts a vacuum pump 1 of the type disclosed in the aforesaid patents, with a length of tubing 2 connecting the pump 1 to an entirely enclosed vacuum vessel 3. A vacuum release 4 according to the present invention is connected to the vessel 3. As more fully described in U.S. Pat. No. 4,806,084 and the other patents, the pump 1 comprises fixed and movable handles 5,6 which can be squeezed together to operate a piston (not shown) within a cylinder 7. This motion of the piston causes air to be drawn from the vessel 3, through the tubing 2, through an inlet port 8 into the cylinder 7, and then to be released through an exhaust port 9. Also depicted as attached to the pump is a pump vacuum release 10 and a vacuum gauge 11 which are more fully described in one or more of the aforesaid patents, and a tubing remover 12.

Referring to FIG. 2, the vacuum release 4 is attached to a vacuum vessel 3. The basic components of the vacuum release 4 are a base 20, a plunger 21 and a rocker 22. The base 20 fits snugly into an opening 33 in a wall 26 of the vessel 3, and has a channel 36 which communicates through the wall 26. The plunger 21 is disposed within the channel 36, and has two passageways 42, 43 to facilitate air flow within the channel 36. The rocker 22 causes the plunger 21 to reciprocate within the channel 36 between a closed position depicted by solid lines 21a and an open position depicted by dashed lines 21b. When the plunger 21 is in the closed position 21a air cannot travel through the channel 36, and a vacuum can be maintained within the vessel 3. When the plunger 21 is in the open position 21b, air can travel through the channel 36 along the passageways 42, 43, and the vacuum is released.

Referring now to FIG. 2 in more detail, the base 20 has an upper surface 30 (depicted to the right in FIG. 2) and a lower surface 31 (depicted to the left in FIG. 2). Extending from the lower surface 31 of the base 20 is a collar 32 which fits snugly into the opening 33 in the wall 26 of the vessel 3. Surrounding the collar 32, at the junction of the collar 32 with the base 20, is a first support 34. A second support 35 extends from the lower surface 31 of the base 20 at the other end of the base 20 from the collar 32. The snug fit of the collar 32 in the opening 33, and the two supports 34, 35 serve to stabilize the position of the base 20 on the vessel 3. The channel 36 communicates between the upper surface 30 and the lower surface 31, and extends through the collar 32.

The plunger 21 has an upper portion 37, a shoulder 38, and a lower portion 39. The lower portion 39 has a notch 40 onto which is fitted a clip 25. Between the clip 25 and the lower surface 31 of the base 3 is a spring 24. In the closed position 21a, the spring 24 compresses an "O" ring 23 situated between the upper surface 30 of the base 20 and the shoulder 38, thereby sealing off the passageways 42, 43.

The rocker 22 has two arms, an actuating arm 45 and a trigger arm 46. The actuating arm 45 extends through a slot 41 in the upper portion 37 of the plunger 21. The trigger arm 46 has a platform 47 for applying finger pressure to the rocker 22. Between the two arms 45, 46 is a pivot 49 having a notch 50. The notch 50 is clipped onto a perch 51 lying within a hollow 52 in the base 20, thereby allowing the rocker 22 to reciprocate between an up position depicted by solid lines 22a, and a down position depicted by dashed lines 22b. Two wings 53, (only one of which is depicted in FIG. 2), extend perpendicularly from the rocker 22, adjacent to the area of contact between the rocker 22 and the perch 51, to provide stability for the rocker 22.

In operation, finger pressure is applied to a platform 47, thereby rocking the rocker 22 to the down position 22b. Because of the pivot 49, the actuating arm 45 thereby pushes the plunger 21 to the open position 21b, and releases the vacuum. An arm stop 48 is interposed between the trigger arm 46 and the base 3, thus limiting the travel of the rocker 22.

Referring to FIG. 3, two passageways 42, 43 are longitudinally disposed along opposite sides of the lower portion 39 of the plunger 21. Other passageway configurations are possible, including having a greater or lesser number of passageways, passageway(s) having curved or other shapes, passageway(s) of equal or unequal dimensions, placement of the passageway(s) at other positions along the plunger or along the channel, and placement of the passageway(s) through a portion of the plunger as opposed to lying on the surface of the plunger. FIG. 3 also depicts a gap 55 between the lower portion 39 of the plunger 21 which mates with the channel 36. The gap 55 permits the plunger 21 to reciprocate freely within the channel 36.

Figure 4:
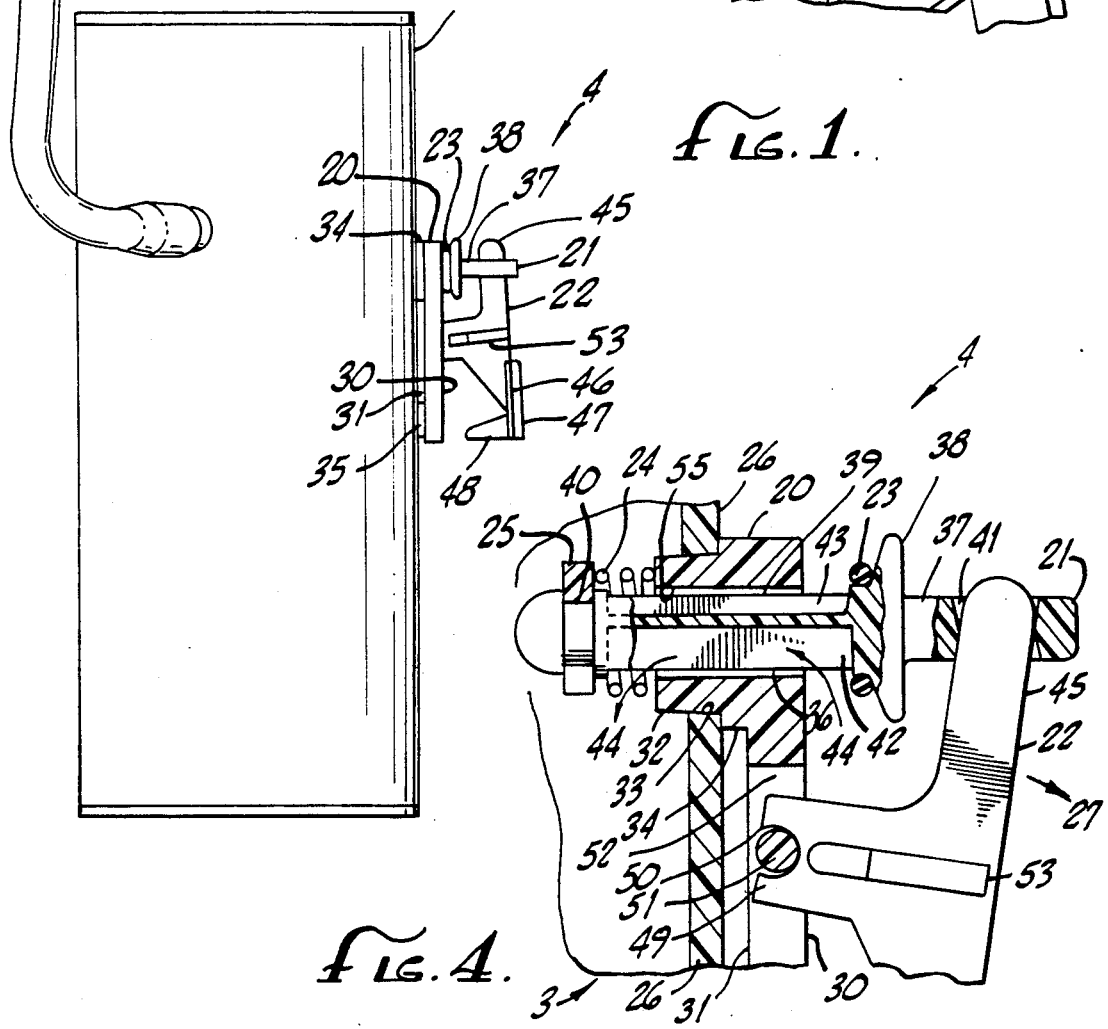
FIG. 4 is a cross sectional view showing the assembled vacuum release in an open position.

Referring to FIG. 4, the direction of motion of the rocker 22 which results in the open position 21b of the plunger 21 is identified by arrow 27. The flow of air along one of the passageways 42 is identified by the arrows 44.

Referring to FIG. 5, a specific embodiment is depicted comprising an open vessel 60, vacuum release 4, and tubing 12. In this embodiment, the open vessel 3 is a medical device which has an open end 61, and is sized and dimensioned to elicit penile erection. The open vessel 60 is capable of containing a vacuum when the open end 61 is covered during use. Preferably, the vacuum release 4 is positioned on the open vessel 3 such that the user can exert finger pressure on the platform 47 to operate the vacuum release 4 while at the same time securely holding the open vessel 3.

I claim:

1. A valve for use with a vessel having a wall with an opening for receiving the valve comprising:
   a base adapted to be frictionally held in the opening and having a channel communicating between a first and a second space defined by the wall;
   a plunger disposed within the channel to reciprocate between an open and a closed position, and having at least one longitudinal passageway through which gas can travel between the first and second spaces when the plunger is in the open position, and through which gas is prevented from traveling between the first and second spaces when the plunger is in the closed position;
   rocker means for reciprocating the plunger between the open and the closed positions, the rocker means sized and dimensioned to be finger operated; and
   the base, plunger and rocker being interconnected such that the vacuum release can be removably attached to the vessel wall as a single unit.

2. An improved vacuum system comprising a vessel and a hand-held vacuum pump, the vessel having at least one wall separating an outside space from an inside space and capable of containing at least a partial vacuum, the wall having an opening between the two spaces, the vacuum pump capable of producing at least a partial vacuum within the vessel, wherein the improvement comprises a vacuum release having:
   a base having a channel fluidly communicating between the inside space and the outside space, he base further having a collar sized and dimensioned to be frictionally held within the opening;

a plunger disposed within the channel to reciprocate between an open and a closed position, the plunger having at least one passageway operatively positioned to allow gas to flow between the outside space and the inside space via the passageway when the plunger is in the open position, the passageway further operatively positioned to prevent gas from flowing between the outside space and the inside space via the passageway when the plunger is in the closed position;

rocker means for reciprocating the plunger between the open and the closed positions, the rocker means sized and dimensioned to be finger operated; and the base, plunger and rocker being interconnected such that the vacuum release can be removably attached to the vessel wall as a single unit.

3. In combination with a vessel having at least one wall separating an outside space from an inside space, said wall having an opening between the two spaces, and said vessel capable of containing at least a partial vacuum, a vacuum release comprising:

a base having a channel fluidly communicating between the inside space and the outside space, the base further having a collar sized and dimensioned to be frictionally held within the opening;

a plunger disposed within the channel to reciprocate between an open and a closed position, the plunger having at least one passageway operatively positioned to facilitate the flow of gas through the passageway from the second space to the first space when the plunger is in the open position, the passageway further operatively positioned to restrict the flow of gas between the outside space and the inside space when the plunger is in the closed position;

rocker means for reciprocating the plunger between the open and the closed positions, the rocker means sized and dimensioned to be finger operated; and the base, plunger and rocker being interconnected such that the vacuum release can be removably attached to the vessel wall as a single unit.

4. The vacuum release of claim 3 wherein the vessel is medical device having an elongated tubular shape for enhancing penile erection.

5. A vacuum release comprising:

a base having a channel communicating between a first space defined by a vessel wall having an opening and a second space, the base further having a collar sized and dimensioned to be frictionally held within the opening;

a plunger disposed within the channel to reciprocate between an open and a closed position, and having at least one longitudinal passageway through which gas can travel between he first and second spaces when the plunger is in the open position, and through which gas is prevented from traveling between the first and second spaces when the plunger is in the closed position;

rocker means for reciprocating the plunger between the open and the closed positions, the rocker means sized and dimensioned to be finger operated; and the base, plunger and rocker being interconnected such that the vacuum release can be removably attached to the vessel wall as a single unit.

6. The vacuum release of claim 5 wherein the plunger has two of said passageways.

7. The vacuum release of claim 5 further comprising: means for biasing the plunger to the closed position.

8. The vacuum release of claim 5 further comprising a rocker and a base, the rocker sized and dimensioned to reciprocate back and forth upon the base.

9. The vacuum release of claim 8 wherein the means for reciprocating comprises:

a perch disposed within the base upon which the rocker rocks back and forth, at least one wing extending perpendicularly from the rocker adjacent to the area of contact between the rocker and the perch, the wings contacting the base to provide stability for the rocker.

10. The vacuum release of claim 8 wherein the means for reciprocating comprises:

the rocker having an actuating arm and a trigger arm, the plunger having a slot, the actuating arm being inserted into the slot, the trigger arm having a platform for exerting finger pressure, and an arm stop extending from the trigger arm opposite the platform, which arm stop presses against the base when the finger pressure exerted upon the trigger arm has moved the plunger into the open position.

* * * * *

UNITED STATES PATENT AND TRADEMARK OFFICE
CERTIFICATE OF CORRECTION

PATENT NO. : 5,112,203

DATED : May 12, 1992

INVENTOR(S) : Theodore C. Neward

It is certified that error appears in the above-identified patent and that said Letters Patent is hereby corrected as shown below:

```
column 4, claim 2, line 66, change "he" to -- the --
column 6, claim 5, line 9, change "he" to -- the --
```

Signed and Sealed this

Thirtieth Day of November, 1993

Attest:

Attesting Officer

BRUCE LEHMAN

Commissioner of Patents and Trademarks